United States Patent [19]

Cragoe, Jr. et al.

[11] 4,237,130
[45] Dec. 2, 1980

[54] 2,3-DIHYDRO-6,7-DISUBSTITUTED-5-(SUBSTITUTED SULFONYL)BENZOFURAN-2-CARBOXYLIC ACIDS

[75] Inventors: Edward J. Cragoe, Jr.; William F. Hoffman, both of Lansdale, Pa.

[73] Assignee: Merck & Co., Inc., Rahway, N.J.

[21] Appl. No.: 50,853

[22] Filed: Jun. 21, 1979

[51] Int. Cl.$^3$ .................. A61K 31/535; C07D 307/84
[52] U.S. Cl. .................................. 424/248.5; 424/267; 424/270; 424/275; 424/285; 544/153; 546/196; 548/129; 548/134; 548/139; 549/60; 260/346.22; 260/346.71; 260/346.73
[58] Field of Search ..................... 260/346.22, 346.71, 260/346.73; 548/134, 139, 129; 549/60; 546/196; 544/153; 424/248.5, 267, 270, 275, 285

[56] References Cited

U.S. PATENT DOCUMENTS 4,087,542  5/1978  Cragoe, Jr. et al. ............. 424/275

OTHER PUBLICATIONS

Wagner and Zook, Synthetic Organic Chemistry, (1953), p. 802.

*Primary Examiner*—Henry R. Jiles
*Assistant Examiner*—Bernard Dentz
*Attorney, Agent, or Firm*—Michael C. Sudol, Jr.; Harry E. Westlake, Jr.

[57] ABSTRACT

The invention relates to 2,3-dihydro-6,7-disubstituted-5-(substituted sulfonyl)benzofuran-2-carboxylic acids and derivatives thereof having diuretic-saluretic, uricosuric and antihypertensive pharmacological activity.

13 Claims, No Drawings

2,3-DIHYDRO-6,7-DISUBSTITUTED-5-(SUBSTITUTED SULFONYL)BENZOFURAN-2-CARBOXYLIC ACIDS

This invention relates to certain benzofurans having diuretic-saluretic, uricosuric and antihypertensive pharmacological activity. Further, this invention relates to processes for the preparation of such compounds; pharmacological compositions comprising such compounds; and to methods of treatment comprising administering such compounds and compositions to patients (both human and animal) for the alleviation of symptoms associated with electrolyte imbalance and fluid retention such as edema associated with hypertension.

The compounds of this invention may be represented by the following generic structure:

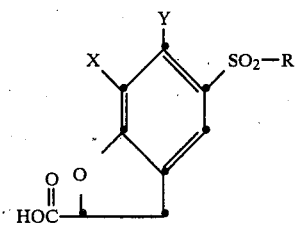

wherein
- X is halo (chloro, fluoro, bromo or iodo), methyl or hydrogen;
- Y is halo (chloro, fluoro, bromo or iodo), methyl or hydrogen.
- X and Y can be joined to form a hydrocarbylene chain containing from 3 to 4 carbon atoms, for example: 1,3-butadienylene:
- R is aryl such as phenyl or mono or disubstituted phenyl wherein the substituent(s) is(are) halo, methyl, trifluoromethyl or methoxy; aralkyl such as benzyl or mono or dinuclear substituted aralkyl wherein the substituent is halo, methyl, methoxy or trifluoromethyl; or a heterocyclic group such as a 5 or 6 membered heterocyclic ring containing one or more atoms of oxygen, sulfur or nitrogen such as 3- or 2-thienyl, 3 or 2-furyl, 1,3,5-thiadiazolyl or substituted heterocyclics as above wherein the substituent is halo or methyl.

Also within the scope of the present invention are the pharmaceutically acceptable salt, ester and amide derivatives of the above described compounds.

For convenience, these compounds will be collectively referred to as "dihydrobenzofuran acids."

The pharmacological studies show that the instant products are effective diuretic, saluretic and uricosuric agents which can be used in the treatment of conditions associated with electrolyte and fluid retention in the treatment of hypertension. These compounds are able to maintain the uric acid concentration in the body at pretreatment levels or to even effect a decrease in the uric acid concentration when administered in therapeutic dosages in conventional vehicles.

Many of the presently available diuretics and saluretics have a tendecny upon administration to induce hyperuricemia which may precipitate uric acid or sodium urate or both in the body which may cause from mild to severe cases of gout. The instant compounds of this invention now provide an effective tool to treat those patients (which includes humans and animals) requiring diuretic and saluretic treatment without incurring the risk of inducing gout. In fact, when used in appropriate doses, the compounds of this invention function as uricosuric agents.

Thus it is an object of the present invention to provide the benzofurans of the above general description and to provide processes for preparation of such compounds. Further objects of this invention are to provide pharmaceutical compositions comprising such benzofurans and to provide methods of treatment comprising administering such compounds and compositions.

DETAILED DESCRIPTION OF THE INVENTION

For purposes of description the benzofurans of the present invention (Formula I above) may be represented according to the following structural formula:

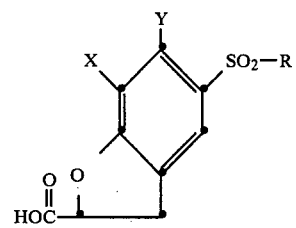

wherein X, Y and R are as previously defined.

The preferred benzofurans of the present invention are those compounds of Formula I wherein X is halo, preferably chloro, or methyl and Y is halo, preferably chloro or methyl, and the pharmaceutically acceptable salts, ester and amide derivatives thereof.

More preferred benzofurans of the present invention are those preferred compounds of Formula I wherein R is

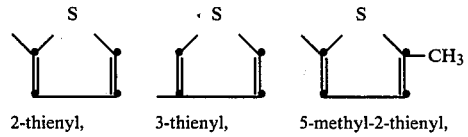

2-thienyl,    3-thienyl,    5-methyl-2-thienyl,

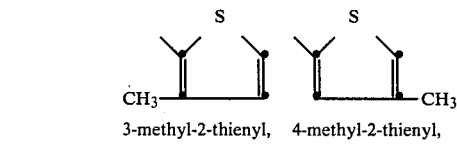

3-methyl-2-thienyl,    4-methyl-2-thienyl,

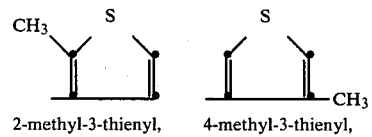

2-methyl-3-thienyl,    4-methyl-3-thienyl,

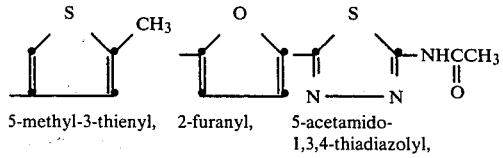

5-methyl-3-thienyl,    2-furanyl,    5-acetamido-1,3,4-thiadiazolyl,

-continued

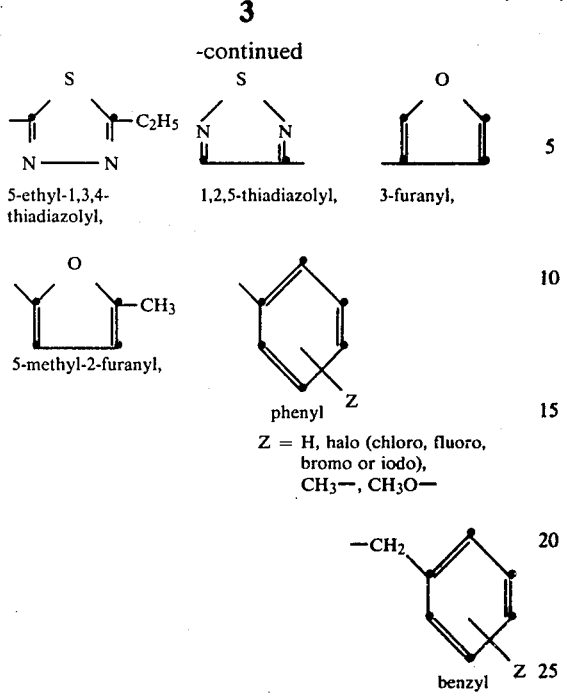

5-ethyl-1,3,4-thiadiazolyl,  1,2,5-thiadiazolyl,  3-furanyl, 5-methyl-2-furanyl, phenyl Z = H, halo (chloro, fluoro, bromo or iodo), CH₃—, CH₃O— benzyl and X and Y are as defined above.

Still more preferred benzofurans of the present invention are those compounds of Formula II below:

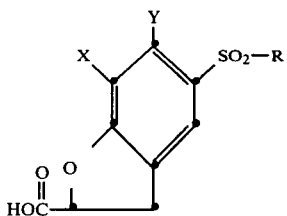

II wherein
X is chloro and
Y is chloro, and
R is as defined for the more preferred benzofurans above, and the pharmacologically acceptable salts, and lower alkyl ester derivatives thereof.

A still more preferred aspect of the invention are those compounds of Formula II wherein X and Y are both chloro and R is

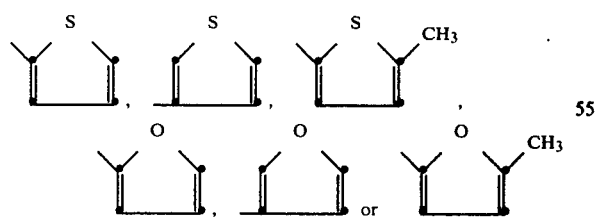

and the pharmaceutically acceptable salts, and lower alkyl ester derivatives thereof.

Several examples of specific compounds of this invention are:

6,7-dichloro-2,3-dihydro-5-(2-thienylsulfonyl)benzofuran-2-carboxylic acid;
6,7-dichloro-2,3-dihydro-5-(3-methyl-2-thienylsulfonyl)benzofuran-2-carboxylic acid;
6,7-dichloro-2,3-dihydro-5-(5-methyl-2-thienylsulfonyl)benzofuran-2-carboxylic acid;
6,7-dichloro-2,3-dihydro-5-(3-thienylsulfonyl)benzofuran-2-carboxylic acid;
6,7-dichloro-2,3-dihydro-5-(2-methyl-3-thienylsulfonyl)benzofuran-2-carboxylic acid;
6,7-dichloro-2,3-dihydro-5-(4-methyl-3-thienylsulfonyl)benzofuran-2-carboxylic acid;
6,7-dichloro-2,3-dihydro-5-(5-methyl-3-thienylsulfonyl)benzofuran-2-carboxylic acid;
6,7-dichloro-2,3-dihydro-5-(2-furanylsulfonyl)benzofuran-2-carboxylic acid;
6,7-dichloro-2,3-dihydro-5-(3-furanylsulfonyl)benzofuran-2-carboxylic acid;
6,7-dichloro-2,3-dihydro-5-(5-acetamido-1,3,4-thiadiazolyl-2-sulfonyl)benzofuran-2-carboxylic acid;
6,7-dichloro-2,3-dihydro-5-(5-ethyl-1,3,4-thiadiazolyl-2-sulfonyl)benzofuran-2-carboxylic acid;
6,7-dichloro-2,3-dihydro-5-(phenylsulfonyl)benzofuran-2-carboxylic acid;
6,7-dichloro-2,3-dihydro-5-(4-chlorophenylsulfonyl)benzofuran-2-carboxylic acid;
6,7-dichloro-2,3-dihydro-5-(4-fluorophenylsulfonyl)benzofuran-2-carboxylic acid;
6,7-dichloro-2,3-dihydro-5-(4-methylphenylsulfonyl)benzofuran-2-carboxylic acid;
6,7-dichloro-2,3-dihydro-5-(3-chlorophenylsulfonyl)benzofuran-2-carboxylic acid;
6,7-dichloro-2,3-dihydro-5-(2-chlorophenylsulfonyl)benzofuran-2-carboxylic acid;
6,7-dichloro-2,3-dihydro-5-(phenylmethylsulfonyl)benzofuran-2-carboxylic acid;
6,7-dichloro-2,3-dihydro-5-(4-methylphenylmethylsulfonyl)benzofuran-2-carboxylic acid;
6,7-dichloro-2,3-dihydro-5-(1,2,5-thiadiazolyl-3-sulfonyl)benzofuran-2-carboxylic acid;
6,7-dichloro-2,3-dihydro-5-(4-methoxyphenylsulfonyl)benzofuran-2-carboxylic acid.

The preferred groups of compounds depicted above have especially good diuretic, saluretic, uricosuric and antihypertensive pharmacological activity.

The benzofurans of the present invention may be prepared essentially by the reaction scheme shown below:

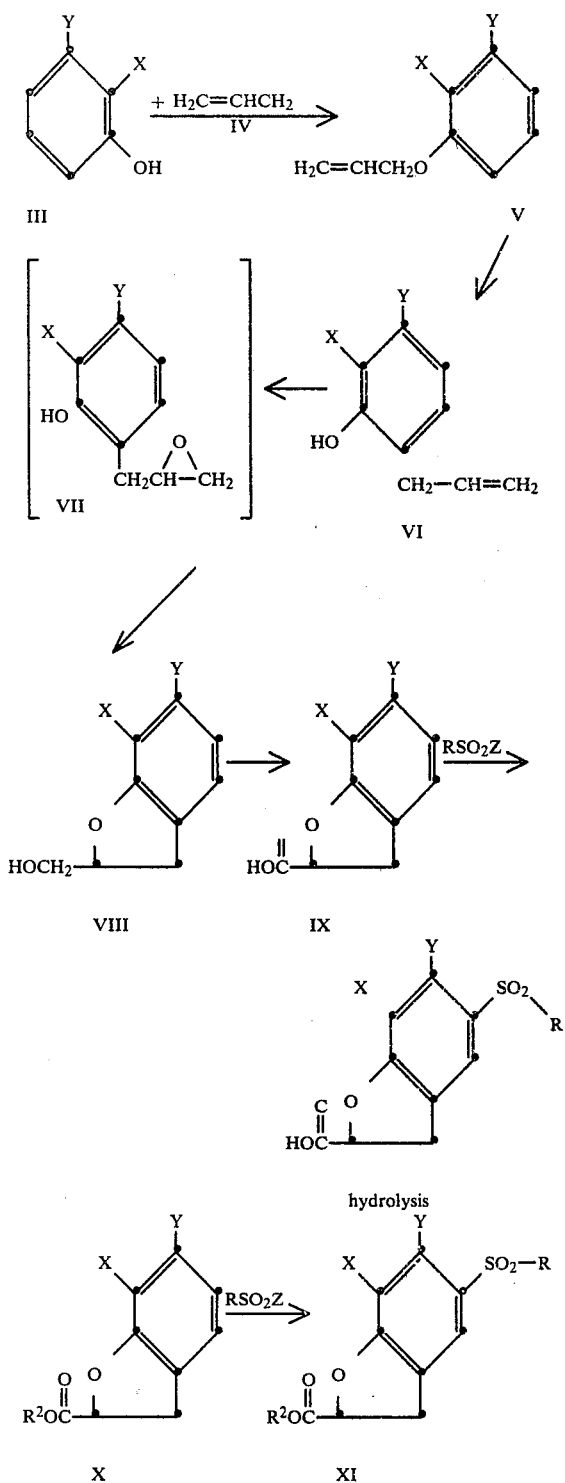

wherein X, Y and R are as defined, Z is halo and $R^2$ is lower alkyl ($C_{1-4}$).

In this reaction scheme, a 2,3-disubstituted-phenol (III) is treated with allyl bromide to yield the corresponding allyl ether (V). Typically the allyl bromide is employed in excess; in fact, it may serve as the reaction solvent. Other solvents, provided they are compatible with the desired course of reaction may be employed, for example, ethanol, dimethylformamide and the like.

Typically the reaction is conducted in the presence of a base such as sodium alkoxide, potassium carbonate and the like at a temperature in the range of from about 25° to about 100° C. and is substantially complete in from about 0.5 to about 2 hours. The Claisen rearrangement to obtain the 6 allyl compound (Formula VI) is effected by heating the reaction mixture at from about 100° to 220° C. The benzofuran nucleus (VIII) is obtained from the 4-allyl compound (VI) by treatment with a peracid such as m-chloroperbenzoic, peracetic acid and the like in a solvent such as methylene chloride, chloroform, acetic acid and the like at a temperature of from about 0° C. to the reflux temperature of the solvent wherein the epoxide (VII) which is initially formed cyclizes to (VIII). There are brackets around the epoxide of Formula (VII) to indicate that it is most generally not isolated and is an intermediate in this particular reaction step. Oxidation of the resulting hydroxymethyl-substituted-benzofuran (VIII) yields the benzofurancarboxylic acid (IX).

Typically this oxidation is effected by oxidizing agents such as chromic acid, potassium permanganate and the like; the temperature of the reaction being typically in the range of from about 0° C. to the reflux temperature of the solvent which is used.

The solvent can be any inert solvent that is not effected by the reaction.

Finally the benzofurancarboxylic acid compound (Formula IX) is converted to the dihydrobenzofurancarboxylic acid compounds of the instant invention (Formula I) by reacting said compound (Formula IX) or its lower alkyl ($C_{1-4}$) ester (X) under Friedel-Crafts conditions with a sulfonyl halide of the formula:

$$RSO_2Z$$

wherein

R has been previously defined and

Z is halogen such as chloro or bromo to yield the desired product directly or by hydrolysis of the resultant ester XI. The lower alkyl ester X can be prepared from the acid IX by known esterification procedures. Suitable catalysts for the Friedel-Crafts type reaction on compounds of formula IX are aluminum chloride, tin, (IV) tetrachloride and the like. The reaction solvent and temperature are not critical inasmuch as any solvent which is inert to the sulfonyl halide/benzofuran reactants may be employed. In this regard, suitable solvents include aliphatic and cycloaliphatic hydrocarbons such as heptane, cyclohexane, and the like; nitrohydrocarbons such as nitrobenzene and the like; and halogenated hydrocarbons such as carbon tetrachloride, mthylene chloride, and the like are employable. The reaction is generally run until formation of the desired product (I) is complete, preferably from about 1 to 24 hours.

Typically the reaction is conducted from 0° C. to the reflux temperature of the particular solvent employed but temperatures up to about 100° maximum may be employed. Applicants have found that a better yield of final product (I) is obtained from compound IX by using no inert solvent but using a slight excess of the acyl halide.

As previously mentioned, the nontoxic, pharmacologically acceptable salts of the acids of Formula I and II are within the scope of this invention. These salts include those of alkali metals, alkaline earth metals and amines such as ammonia, primary and secondary amines and quaternary ammonium hydroxides. Especially preferred metal cations are those derived from alkali metals, e.g., sodium, potassium, lithium, and the like and alkaline earth metals, e.g., calcium, magnesium, and the like and other metals, e.g., aluminum, iron and zinc.

Pharmaceutically acceptable salts can be formed from ammonia, primary, secondary, or tertiary amines, or quaternary ammonium hydroxides such as methylamine, dimethylamine, trimethylamine, ethylamine, N-methylhexylamine, benzylamine, α-phenethylamine, ethylenediamine, piperidine, 1-methylpiperazine, morpholine, pyrrolidine, 1,4-dimethylpiperazine, ethanolamine, diethanolamine, triethanolamine, tris(hydroxymethyl)aminomethane, N-methylglucamine, N-methylglucosamine, ephedrine, procaine, teramethylammonium hydroxide, tetrethylammonium hydroxide, benzyltrimethylammonium and the like. These salts are particularly useful as parenteral solutions because they are very soluble in pharmaceutical carriers such as water or alcohol.

Also included within the scope of this invention are the ester and amide derivatives of the instant products which are prepared by conventional methods well known to those skilled in the art. Thus, for example, the ester derivative may be prepared by the reaction of an dihydrobenzofuran-2-carboxylic acid of this invention with an alcohol, for example, with a lower alkanol such as methanol or ethanol. The amide derivatives may be prepared by converting the same acid to its corresponding acid chloride by treatment with thionyl chloride followed by treating said acid chloride with ammonia, an appropriate mono-lower alkylamine, di-lower alkyl amine or a hetero amine, such as piperidine, morpholine and the like, to produce the corresponding amide compound. These and other equivalent methods for the preparation of the ester and amide derivatives of the instant products will be apparent to one having ordinary skill in the art and to the extent that said derivatives are both non-toxic and physiologically acceptable to the body system, said derivatives are the functional equivalent of the corresponding free acids of the present invention.

Of the non-toxic pharmaceutically acceptable salt, ester and amide derivatives of Formulae I and II, the preferred salts are those of ammonia, amines and of the alkali metals—principally sodium and potassium; the preferred esters are those derived from lower alkanols having from 1 to about 6 carbon atoms; the preferred amides are those derived from mono- and di-lower alkyl amines and hetero amines such as piperidine, morpholine and the like.

The instant compounds disclosed herein contain an asymmetric carbon atom at position 2 of the benzofuran ring. The enantiomers may be separated by methods well known to those skilled in the art. This invention, therefore, embraces not only the racemic benzofurans but also the optically active enantiomers. In general, the pure enantiomers are prepared by fractional crystallization of salts of the racemic acids derived from optically active amines followed by generation of the free acid of the enantiomer by addition of an equimolar amount of a strong acid such as hydrochloric acid.

Although diuretics are often live-saving because of the above beneficial therapeutic effects, most of them have the disadvantage of causing the excretion of appreciable amounts of potassium ions. When an excessive loss of potassium ions occurs, a severe muscular weakness and feeling of extreme physical exhaustion results. The patient eliminates the unwanted sodium ions due to the action of the diuretic drugs but the undesired elimination of the potassium ions produces an imbalance that should not be allowed to persist.

This invention also involves co-administration of a dihydrobenzofurancarboxylic acid with a pyrazinoylguanidine either in the form of a salt and/or as a mixture with a hydrochloride salt of pyrazinoylguanidine, to thereby prevent the elimination of excessive amount of potassium ions without altering or actually increasing the amount of sodium ions that are eliminated.

To achieve the beneficial results of this invention, the preferred pyrazinoylguanidine compound is N-amidino-3,5-diamino-6-chloropyrazinecarboxamide (amiloride) or its hydrochloride salt (amiloride hydrochloride) which is described in the literature and patented arts.

Another advantage of the N-amidino-3,5-diamino-6-chloropyrazinecarboxamide salts of the dihydrobenzofurancarboxylic acid diuretics is their insolubility which make the salts' gastrointestinal absorption slower and more gradual providing a chemical method of achieving the same effect as microencapsulation.

The examples which follow illustrate the benzofuran products of the present invention and the methods by which they are prepared. However, the examples are illustrative only and it will be apparent to those having ordinary skill in the art that all the products embraced by the above-given description of the present invention may also be prepared in an analogous manner by substituting the appropriate starting materials for those set forth in the examples.

EXAMPLE 1

6,7-Dichloro-2,3-dihydro-5-(2-thienylsulfonyl)benzofuran-2-carboxylic acid Hemihydrate To a well stirred mixture of ethyl 6,7-dichloro-2,3-dihydrobenzofuran-2-carboxylate (5.2 g) and 2-thienylsulfonyl chloride (3.6 g) protected from the atmosphere with a calcium chloride tube is added the anhydrous aluminum chloride (2.6 g) over a five minute period. The reaction mixture is stirred at 25° C. for 18 hours and at 90° C. for one hour, then poured into ice water (150 ml) and hydrochloric acid (15 ml). The esterified product is extracted into ether, washed with brine, dried over magnesium sulfate and the ether distilled at reduced pressure. The residue is warmed (80° C.) in 10% NaOH (100 ml) for one hour to obtain a solution which is acidified with hydrochloric acid (25 ml) to obtain the product as a viscous oil. The product is extracted into ether, washed with brine, dried over magnesium sulfate and the ether distilled at reduced pressure. The 6,7-dichloro-2,3-dihydro-5-(2-thienylsulfonylbenzofuran-2-carboxylic acid hemihydrate melts at 189°–193° C. after purification by column chromatography.

Elemental Analysis for $C_{13}H_8Cl_2O_5S_2 \cdot \frac{1}{2}H_2O$
Calc: C, 40.21; H, 2.33
Found: C, 40.52; H, 2.36

EXAMPLE 2

Using the method of Example 1 except that the 2-thienylsulfonyl chloride is substituted by an equimolar amount of:
3-methyl-2-thienylsulfonyl chloride
4-methyl-2-thienylsulfonyl chloride
5-methyl-2-thienylsulfonyl chloride
3-thienylsulfonyl chloride
2-methyl-3-thienylsulfonyl chloride
4-methyl-3-thienylsulfonyl chloride 5-methyl-3-thienylsulfonyl chloride
2-furanylsulfonyl chloride
3-furanylsulfonyl chloride
5-acetamido-1,3,4-thiadiazolyl-2-sulfonyl chloride
5-ethyl 1,3,4-thiadiazolyl-2-sulfonyl chloride phenylsulfonyl chloride
4-chlorophenylsulfonyl chloride
4-fluorophenylsulfonyl chloride
4-methylphenylsulfonyl chloride
3-chlorophenylsulfonyl chloride
2-chlorophenylsulfonyl chloride
phenylmethylsulfonyl chloride
4-methylphenylmethylsulfonyl chloride
1,2,4-thiadiazolyl-3-sulfonyl chloride
4-methoxyphenylsulfonyl chloride
and carrying out the reaction as described in Example 1. There is obtained:
6,7-dichloro-2,3-dihydro-5-(3-methyl-2-thienylsulfonyl)benzofuran-2-carboxylic acid
6,7-dichloro-2,3-dihydro-5-(4-methyl-2-thienylsulfonyl)benzofuran-2-carboxylic acid
6,7-dichloro-2,3-dihydro-5-(5-methyl-2-thienylsulfonyl)benzofuran-2-carboxylic acid
6,7-dichloro-2,3-dihydro-5-(3-thienylsulfonyl)benzofuran-2-carboxylic acid
6,7-dichloro-2,3-dihydro-5-(2-methyl-3-thienylsulfonyl)benzofuran-2-carboxylic acid
6,7-dichloro-2,3-dihydro-5-(4-methyl-3-thienylsulfonyl)benzofuran-2-carboxylic acid
6,7-dichloro-2,3-dihydro-5-(5-methyl-3-thienylsulfonyl)benzofuran-2-carboxylic acid
6,7-dichloro-2,3-dihydro-5-(2-furanylsulfonyl)benzofuran-2-carboxylic acid
6,7-dichloro-2,3-dihydro-5-(3-furanylsulfonyl)benzofuran-2-carboxylic acid
6,7-dichloro-2,3-dihydro-5-(5-acetamido-1,4,5-thiadiazolyl-2-sulfonyl)benzofuran-2-carboxylic acid
6,7-dichloro-2,3-dihydro-5-(5-methyl-1,3,4-thiadiazolyl-2-sulfonyl)benzofuran-2-carboxylic acid
6,7-dichloro-2,3-dihydro-5-(phenylsulfonyl)benzofuran-2-carboxylic acid
6,7-dichloro-2,3-dihydro-5-(4-chlorophenylsulfonyl)-benzofuran-2-carboxylic acid
6,7-dichloro-2,3-dihydro-5-(5-fluorophenylsulfonyl)-benzofuran-2-carboxylic acid
6,7-dichloro-2,3-dihydro-5-(4-methylphenylsulfonyl)-benzofuran-2-carboxylic acid
6,7-dichloro-2,3-dihydro-5-(3-chlorophenylsulfonyl)-benzofuran-2-carboxylic acid
6,7-dichloro-2,3-dihydro-5-(2-chlorophenylsulfonyl)-benzofuran-2-carboxylic acid
6,7-dichloro-2,3-dihydro-5-(phenylmethylsulfonyl)-benzofuran-2-carboxylic acid
6,7-dichloro-2,3-dihydro-5-(4-methylphenylmethylsulfonyl)benzofuran-2-carboxylic acid
6,7-dichloro-2,3-dihydro-5-(1,2,4-thiadiazolyl-3-sulfonyl)benzofuran-2-carboxylic acid
6,7-dichloro-2,3-dihydro-5-(4-methoxyphenylsulfonyl)-benzofuran-2-carboxylic acid

EXAMPLE 3

Using the method of Example 1 except that the ethyl, 6,7-dichloro-2,3-dihydrobenzofuran-2-carboxylate is substituted by a equimolar amount of ethyl 6,7-dimethyl-2,3-dihydrobenzofuran-2-carboxylate and carrying out the reaction as described in Example 1, there is obtained 6,7-dimethyl-2,3-dihydro-5-(2-thienylsulfonyl)benzofuran-2-carboxylic acid.

As mentioned previously, the novel compounds of this invention are diuretic and saluretic agents. When administered to patients in therapeutic dosages in conventional vehicles, the instant products effectively reduce the amount of sodium and chloride ions in the body, lower dangerous excesses of fluid levels to acceptable levels and in general, alleviate conditions usually associated with ederma or fluid retention.

Also as mentioned previously, these compounds are able to maintain the uric acid concentration in the blood at pretreatment levels or even cause a decrease in uric acid concentration. The presence of excess uric acid in the blood can lead to crystallization of uric acid and uric acid salts in the joints causing gout. In addition hyperuricemia in conjunction with hyperlipidemia has been implicated in increasing the risk of sustaining cardiovascular heart disease.

The compounds of this invention can be administered to patients (both animal and human) as the racemic form, as either enantiomer or in a wide variety of mixtures of various ratios of the two enantiomers, each of which may be given in any of a variety of therapeutic dosages in conventional vehicles as, for example, by oral administration in the form of a tablet or by intravenous injection. In addition, the compounds may be formulated into suppositories or as a salve for topical administration or they may be administered sublinqually. Also, the daily dosage of the products may be varied over a wide range as for example, in the form of scored tablets containing 0.25, 1, 5, 10, 25, 50, 100, 150, 200, 250, and 500 milligrams of the active ingredient for the symptomatic adjustment of the dosage to the patient to be treated. These dosages are well below the toxic or lethal dose of the products.

A suitable unit dosage form of the product of this invention can be administered by mixing 100 mg. of a dihydrobenzofuran or a suitable salt, ester or amide derivative thereof of the present invention with 99 mg. of lactose and 1 mg. of magnesium sterate and placing the 200 mg. mixture into a No. 1 gelatin capsule. Similarly by employing more of the active ingredient and less lactose, other dosage forms can be put up in No. 1 gelatin capsules and should it be necessary to mix more than 200 mg. of ingredients together larger capsules may be employed. Compressed tablets, pills or other desired unit dosages can be prepared to incorporate the compounds of this invention by conventional methods and if desired can be made up as elixirs or as injectable solutions by methods well known to pharmacists.

An effective amount of the product is ordinarily supplied at a unit dosage level of from about 0.003 mg. to about 10 mg./kg. of body weight of the patient. Preferably the range is from about 0.01 mg. to about 1.5 mg./kg. with a most preferred dose being about 0.07 to 0.35 mg./kg. of body weight. The unit dose can be administered as infrequently as twice per week to as frequently as 3 times per day.

It is also within the scope of this invention to combine two or more of the compounds of this invention into a unit dosage form or to combine one or more of the compounds of this invention with other known diuretics and saluretics or with other desired therapeutic and/or nutritive agents in dosage unit form.

The present invention embraces such compositions administration to patients, preferably by oral administration, wherein the potassium conserving diuretic, N-amidino-3,5-diamino-6-chloropyrazinecarboxamide hydrochloride, hereinafter referred to as amiloride hydrochloride, is present as a physical mixture in combination with the dihydrobenzofurans of the present invention. The present invention embraces compositions wherein the molar ratio of the dihydrobenzofuran to amiloride hydrochloride ranges from about 50:1 to 1:1. The preferred ratios of the dihydrobenzofuran to amiloride hydrochloride ranges from 25:1 to 1:1.

EXAMPLE 4

Dry-filled capsules containing 100 mg. of active ingredients per capsule

|  | Per Capsule |
| --- | --- |
| 6,7-Dichloro-2,3-dihydro-5(2-thienylsulfonyl)benzofuran-2-carboxylic acid | 100 mg. |
| Lactose | 99 mg. |
| Magnesium sterate | 1 mg. |
| Capsule (Size No. 1) | 200 mg. |

The 6,7-dichloro-2,3-dihydro-5-(2-thienylsulfonyl)benzofuran-2-carboxylic acid is reduced to a No. 60 powder and then lactose and magnesium sterate are passed through a No. 60 bolting cloth onto the powder and the combined ingredients admixed for 10 minutes and then filled into a No. 1 dry gelatin capsule.

Similar dry-filled capsules are prepared by replacing the active ingredient of the above example by the sodium, diethanolamine, and triethanolamine salt thereof, respectively.

Similarly dry filled capsules can be prepared by replacing the active ingredient of the above example by a molar equivalent amount of any of the other novel compounds of this invention.

Following the procedure for combining the ingredients as described in Example 4, the following dry filled capsules can be prepared:

EXAMPLE 5

Dry-filled capsules containing 100 mg. of dihydrobenzofuran and 10 mg. of amilamide hydrochloride dihydrate per capsule

|  | Per Capsule |
| --- | --- |
| 6,7-Dichloro-2,3-dihydro-5(2-thienylsulfonyl)benzofuran-2-carboxylic acid | 100 mg. |
| N-Amidino-3,5-diamino-6-chloro-pyrazine carboxamide hydrochloride dihydrate | 10 mg. |
| Lactose | 89 mg. |
| Magnesium sterate | 1 mg. |
| Capsule (Size No. 1) | 200 mg. |

What is claimed is:

1. A compound of the formula:

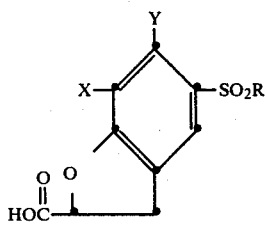

wherein

X is halo, methyl or hydrogen
Y is halo, methyl or hydrogen
X and Y can be combined to form a hydrocarbylene radical of from 3 to 4 carbon atoms;
R is selected from the group consisting of
2-thienyl, 3-thienyl, 5-methyl-2-thienyl
3-methyl-2-thienyl,
4-methyl-2-thienyl, 2-methyl-3-thienyl
4-methyl-3-thienyl, 5-methyl-3-thienyl
5-acetamido-1,3,4-thiadiazolyl, 5-ethyl-1,2,4-thiadiazolyl, 1,2,5-thiadiazolyl, 2-furanyl,
3-furanyl, 5-methyl-2-furyl, phenyl or substituted phenyl wherein the substituent is halo, methyl; trifluoromethyl or methoxy, benzyl or substituted benzyl wherein the substituent is halo, methyl, methoxy or trifluoromethyl and the non-toxic pharmaceutically acceptable salt, lower alkyl ester and amino, loweralkylamino, diloweralkylamino, piperidino or morpholino derivative thereof.

2. The compound of claim 1 wherein X and Y are both chloro and the pharmaceutically acceptable salt and lower alkyl ester derivative thereof.

3. A compound of claim 2 wherein X and Y are chloro and R is 2-thienyl, 3-thienyl, 5-methyl-2-thienyl, 2-furyl, 3-furyl or 5-methyl-2-furyl.

4. The (+) and (−) isomers of the compound of claim 2.

5. The compound of claim 1 wherein X and Y are chloro and R is 2-thienyl thus forming 6,7-dichloro-2,3-dihydro-5-(2-thienylsulfonyl)benzofuran-2-carboxylic acid.

6. The (+) enantiomer of the compound of claim 5.

7. The (−) enantiomer of the compound of claim 5.

8. A mixture of 1 part (+) enantiomer of the compound of claim 5 with 2 to 4 parts of the (−) enantiomer of the compound of claim 5.

9. The compound of claim 1 wherein X and Y are chloro and R is 2-furanyl thus forming 2,3-dihydro-6,7-dimethyl-5-(furanylsulfonyl)benzofuran-2-carboxylic acid.

10. A pharmaceutical composition useful in the treatment of edema associated with hypertension comprising a therapeutically effective amount of a compound of the formula:

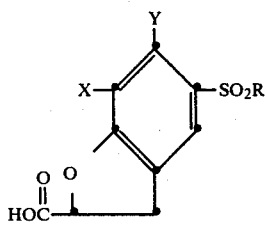

wherein
X is chloro;
Y is chloro; and
R is selected from the group consisting of
2-thienyl, 3-thienyl, 5-methyl-2-thienyl
3-methyl-2-thienyl,
4-methyl-2-thienyl, 2-methyl-3-thienyl
4-methyl-3-thienyl, 5-methyl-3-thienyl
5-acetamido-1,3,4-thiadiazolyl, 5-ethyl-1,2,4-thiadiazolyl, 1,2,5-thiadiazolyl, 2-furanyl,
3-furanyl, 5-methyl-2-furyl, phenyl or substituted phenyl wherein the substituent is halo, methyl; trifluoromethyl or methoxy benzyl or substituted benzyl wherein the substituent is halo, methyl, methoxy or trifluoromethyl and the non-toxic pharmaceutically acceptable salt, lower alkyl ester and amino, loweralkylamino, diloweralkylamino, piperidino or morpholino derivative thereof and a pharmaceutically acceptable carrier.

11. A pharmaceutical composition of claim 10 wherein the said compound is 6,7-dichloro-2,3-dihydro-5-(2-thienylsulfonyl)benzofuran-2-carboxylic acid.

12. A pharmaceutical composition of claim 10 wherein the said compound is 6,7-dichloro-2,3-dihydro-5-(2-furanylsulfonyl)benzofuran-2-carboxylic acid.

13. A method of treatment of edema associated with hypertension comprising the administration of a therapeutically effective amount in unitary dosage of a compound having the formula of:

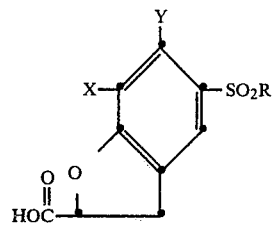

wherein
X is halo, methyl or hydrogen
Y is halo, methyl or hydrogen
X and Y can be combined to form a hydrocarbylene radical of from 3 to 4 carbon atoms;
R is selected from the group consisting of
2-thienyl, 3-thienyl, 5-methyl-2-thienyl, 3-methyl-2-thienyl, 4-methyl-2-thienyl, 2-methyl-3-thienyl,
4-methyl-3-thienyl, 5-methyl-3-thienyl,
5-acetamido-1,3,4-thiadiazolyl, 5-ethyl-1,2,4-thiadiazolyl, 1,2,5-thiadiazolyl, 2-furanyl,
3-furanyl, 5-methyl-2-furyl, phenyl or substituted phenyl wherein the substituent is halo, methyl; trifluoromethyl or methoxy, benzyl or substituted benzyl wherein the substituent is halo, methyl, methoxy or trifluoromethyl, and
the non-toxic pharmaceutically acceptable salt, lower alkyl ester and amino, loweralkylamino, diloweralkylamino, piperidino or morpholino derivative thereof.

* * * * *